United States Patent [19]

Nohira et al.

[11] 4,376,213

[45] Mar. 8, 1983

[54] METHOD FOR OPTICAL RESOLUTION OF 2-(4-CHLOROPHENYL)-3-METHYL-BUTANOIC ACID

[75] Inventors: Hiroyuki Nohira, Urawa; Daiyo Terunuma, Oomiya; Shinji Koube, Tokyo, all of Japan

[73] Assignee: Sumitomo Chemical Company, Limited, Osaka, Japan

[21] Appl. No.: 344,523

[22] Filed: Feb. 1, 1982

[30] Foreign Application Priority Data

Mar. 6, 1981 [JP] Japan .................................. 56-31248

[51] Int. Cl.³ ............................................. C07B 19/00
[52] U.S. Cl. .................................... 562/401; 562/402; 562/496
[58] Field of Search ....................... 562/401, 402, 496

[56] References Cited

U.S. PATENT DOCUMENTS 3,405,159 10/1968 Krieger et al. ................. 562/402 X
3,450,751 6/1969 Noyori et al. ....................... 562/402
4,230,860 10/1980 Raghu ............................. 562/401 X
4,245,116 1/1981 Ohno et al. ......................... 562/401

Primary Examiner—Natalie Trousof
Assistant Examiner—Vera C. Clarke
Attorney, Agent, or Firm—Birch, Stewart, Kolasch & Birch

[57] ABSTRACT

A method for optical resolution of 2-(4-chlorophenyl)-3-methylbutanoic acid, which comprises crystallizing out the salt between (+) or (−)-2-(4-chlorophenyl)-3-methylbutanoic acid and diethylamine in a molar proportion of 2:1 predominantly from a super-saturated solution of the salt of 2-(4-chlorophenyl)-3-methylbutanoic acid with diethylamine, collecting the crystallized salt and decomposing the collected salt under acidic conditions to obtain the corresponding optically active acid.

6 Claims, No Drawings

METHOD FOR OPTICAL RESOLUTION OF 2-(4-CHLOROPHENYL)-3-METHYLBUTANOIC ACID

The present invention relates to a method for optical resolution of 2-(4-chlorophenyl)-3-methylbutanoic acid. More particularly, it relates to a method for optical resolution of 2-(4-chlorophenyl)-3-methylbutanoic acid which comprises crystallizing out predominantly the salt between optically active 2-(4-chlorophenyl)-3-methylbutanoic acid and diethylamine in a molar ratio of 2:1 from a super-saturated solution of the diethylamine salt of 2-(4-chlorophenyl)-3-methylbutanoic acid, collecting the crystallized salt and decomposing the collected salt to obtain optically active 2-(4-chlorophenyl)-3-methylbutanoic acid.

2-(4-Chlorophenyl)-3-methylbutanoic acid (hereinafter referred to as "CPA") is an important substance as the acid component of synthetic pyrethroids. The A$\alpha$-isomer of the phenvalerate of the pyrethroid synthesized by the use of optically active CPA is known to have a potency of 4 to 10 times that of the one synthesized by the use of CPA. Thus, the development of a simple method for optical resolution of CPA has been highly desired.

For optical resolution of CPA, there are known a method using (+) or (−)-phenylethylamine, a method using (+) or (−)-1-phenyl-2-(p-tolyl)ethylamine, etc. These known methods are suitable for obtaining either one of two optical isomers but not suitable for obtaining its antipode, because such antipode can be recovered only through a series of complex operations including decomposition of the diastereomer salt to obtain CPA, formation of its diastereomer salt with a base having an opposite optical activity and fractional crystallization of such salt.

As a result of extensive study, it has been found that the (+) and (−) isomers of CPA can be readily obtained in excellent yields with high purities by crystallizing out predominantly the salt between optically active CPA and diethylamine in a molar proportion of 2:1 (hereinafter referred to as "optically active CPA/diethylamine (2:1) salt") from a super-saturated solution of the diethylamine salt of CPA, collecting the crystallized salt and decomposing the collected salt.

Namely, the method of this invention comprises crystallizing out the (+) or (−)-CPA/diethylamine (2:1) salt predominantly from a super-saturated solution of the diethylamine salt of CPA with or without addition of the seed crystals of the (+) or (−)-CPA/diethylamine (2:1) salt thereto, collecting the crystallized salt therefrom and decomposing the collected salt under acidic conditions to obtain (+) or (−)-CPA.

In carrying out the method of the invention, the salt of (±)-CPA or CPA containing either one of its optically active isomers in an excessive amount with diethylamine in a molar proportion of 1:0.5–1.0 is dissolved in a liquid diluent while heating to make a super-saturated solution. In this case, the salt of CPA with diethylamine as previously prepared may be dissolved into a liquid diluent. Alternatively, CPA and diethylamine may be dissolved into a liquid diluent to make their salt therein. Preferably, the system is so adjusted to include either one of the optically active isomers which is desired to obtain first in an excessive amount, whereby its crystals can be readily separated out.

The addition of the seed crystals to the above prepared super-saturated solution is not essential but favorable. The same kind of the salt of the optically active isomer as that of the optically active isomer as seeded can be separated out. When CPA to be optically resolved contains either one of the optically active isomers in an excessive amount, seeding with the salt of the optically active isomer of the same kind as above is preferred. When the degree of excess is sufficiently large, the salt of the optically active isomer may be crystallized out without seeding.

The mother liquor from which the crystals have been separated may be supplemented with the (±)-CPA/diethylamine (2:1) salt as previously prepared or with (±)-CPA and diethylamine in a molar proportion of 2:1. From the resulting liquor, the salt of the optically active isomer having an opposite optical activity to that as above separated is crystallized out with or without addition of the seed crystals of such salt thereto, followed by its separation.

Subsequently, the above operations are effected with repetition, whereby racemic CPA or CPA having a relatively low optical purity can be optically resolved with ease and perfection in the form of its salt with diethylamine in a molar ratio of 2:1.

In the above operations, the liquid diluent may be the one chosen from water and organic solvents such as methanol, ethanol, 1-propanol, 2-propanol and acetone. Mixtures thereof may be also used.

The optically active CPA/diethylamine (2:1) salt as above obtained may be decomposed with an acid such as hydrochloric acid or sulfuric acid in an aqueous medium, if necessary, after recrystallization for purification. The liberated optically active CPA is extracted with an organic solvent such as ether or benzene, and the extract is concentrated under reduced pressure to obtain (+) or (−)-CPA with a high optical purity.

Different from conventional optical resolution methods wherein different resolving agents are needed depending upon different optical antipodes, the method of this invention can accomplish the optical resolution easily with a single resolving agent. Thus, it is quite advantageous for industrial application.

Some practical embodiments of this invention are illustratively shown in the following Examples.

EXAMPLE 1

(±)-CPA (37 g), diethylamine (12.7 g), (±)-CPA/diethylamine (2:1) salt (3.5 g) and (+)-CPA/diethylamine 2:1) salt (1.5 g) were dissolved in water (150 ml) while heating. The resultant solution was allowed to cool, and when the temperature reached to about 35° C., seed crystals of (+)-CPA/diethylamine (2:1) salt (250 mg) were added thereto. After allowing to stand overnight, the precipitated crystals were collected by filtration to obtain (+)-CPA/diethylamine (2:1) salt (5.96 g). $[\alpha]_{435}^{17}$ +24.9° (c=2, 99% methanol). Optical purity, 81.6% (calculated from the optical rotation of pure (+)-CPA/diethylamine (2:1) salt (M.P., 135°–136.5° C.; $[\alpha]_{435}^{21}$ +30.5° (c=2, 99% methanol)).

To the filtrate after separation of (+)-CPA/diethylamine (2:1) salt, (±)-CPA/diethylamine (2:1) salt (5.5 g) was added, followed by heating to make a solution. The solution was allowed to cool, and when the temperature reached to about 35° C., seed crystals of (−)-CPA/diethylamine (2:1) salt (250 mg) were added thereto. After allowing to stand overnight, the precipitated crystals were collected by filtration to obtain (−)-CPA/diethylamine (2:1) salt. $[\alpha]_{435}^{22}$ −26.0° (c=2, 99% methanol). Optical purity, 85.2% (calculated from the optical rotation of pure (−)-CPA/diethylamine (2:1) salt (M.P., 135°-136.5° C.); $[\alpha]_{435}^{10}$ −30.5° (c=2, 99% methanol).

The above operations were carried out with repetition to obtain (+)-CPA/diethylamine (2:1) salt (5.0–6.0 g) and (−)-CPA/diethylamine (2:1) salt (5.0–6.0 g) alternatively and respectively in optical purities of more than 80%.

The above obtained (+)-CPA/diethylamine (2:1) salt (10.0 g) was recrystallized from a mixture of water and 2-propanol (1:1 by weight) (18 ml) to obtain its purified crystals (7.4 g). Recrystallization yield, 74.0%. $[\alpha]_{435}^{21}$ +30.1° (c=2, 99% methanol). Optical purity, 98.7%.

To the purified salt (7.4 g) as obtained above, 1 N hydrochloric acid (80 ml) and ether (80 ml) were added, followed by stirring for decomposition. After allowing to stand, the water phase and the ether phase were separated. The ether phase was dried over anhydrous sodium sulfate and concentrated to give (+)-CPA (6.06 g). $[\alpha]_D^{11}$ +47.5° (c=2, chloroform). Optical purity, 99.0%. Recovery from the salt, 96.0%.

On the other hand, the above obtained (−)-CPA/diethylamine (2:1) salt (10.0 g) was recrystallized from a mixture of water and 2-propanol (1:1 by weight) (18 ml) to obtain its purified crystals (7.50 g). Recrystallization yield, 75.0%. $[\alpha]_{435}^{24}$ −29.5° (c=2, 99% methanol). Optical purity, 96.7%.

The purified salt (7.5 g) as above obtained was decomposed in the same manner as in the case of (+)-CPA/diethylamine (2:1) salt to give (−)-CPA (6.2 g). $[\alpha]_D^{25}$ −46.9° (c=2, chloroform). Optical purity, 97.7%. Recovery from the salt, 97.0%.

EXAMPLE 2

(±)-CPA (36.2 g), diethylamine (12.4 g), (±)-CPA/diethylamine (2:1) salt (5 g) and (+)-CPA/diethylamine (2:1) salt (1.5 g) were dissolved in water (152 ml) while heating. The resulting solution was cooled with water while stirring, and when the temperature reached to 45° C., seed crystals of (+)-CPA/diethylamine (2:1) salt (250 mg) were added thereto. Cooling was further continued for 3 hours while stirring, and when the temperature reached to about 23° C., the precipitated crystals were collected by filtration to obtain (+)-CPA/diethylamine (2:1) salt (4.38 g). $[\alpha]_{435}^{17}$ +26.3° (c=2, 99% methanol). Optical purity, 86.2%.

To the filtrate, (±)-CPA/diethylamine (2:1) salt (5.5 g) was added, followed by heating to make a solution. The solution was cooled with water, and when the temperature reached to about 45° C., seed crystals of (−)-CPA/diethylamine (2:1) salt (250 mg) were added thereto, followed by cooling while stirring. After 2.5 hours, the temperature reached to 25° C., and the precipitated crystals were collected by filtration to obtain (−)-CPA/diethylamine (2:1) salt. $[\alpha]_{435}^{23}$ −24.9° (c=2, 99% methanol). Optical purity, 81.6%.

The above operations were carried out with repetition to obtain (+)-CPA/diethylamine (2:1) salt (5.0–6.0 g) alternatively and respectively in optical purities of more than 80%.

The above obtained (+)-CPA/diethylamine (2:1) salt (5.7 g) was recrystallized from a mixture of water and 2-propanol (1:1 by weight) (10 ml) to obtain its purified crystals (4.2 g). Recrystallization yield, 73.7%. $[\alpha]_{435}^{21}$ +29.5° (c=2, 99% methanol). Optical purity, 96.7%.

To the purified salt (4.20 g) as obtained above, 1 N hydrochloric acid (50 ml) and ether (50 ml) were added, followed by stirring for decomposition. After allowing to stand, the water phase and the ether phase were separated. The ether phase was dried over anhydrous sodium sulfate and concentrated to give (+)-CPA (3.36 g). $[\alpha]_D^{11}$ +46.9° (c=2, chloroform). Optical purity, 97.7%. Recovery from the salt, 93.7%.

On the other hand, the above obtained (−)-CPA/diethylamine (2:1) salt (5.3 g) was recrystallized from a mixture of water and 2-propanol (1:1 by weight) (10 ml) to obtain its purified crystals (3.90 g). Recrystallization yield, 73.6%. $[\alpha]_{435}^{24}$ −29.1° (c=2, 99% methanol). Optical purity, 95.5%.

The purified salt (3.7 g) as above obtained was decomposed in the same manner as in the case of (+)-CPA/diethylamine (2:1) salt to give (−)-CPA (3.1 g). $[\alpha]_D^{25}$ −46.1° (c=2, chloroform). Optical purity, 96.0%. Recovery from the salt, 98.2%.

EXAMPLE 3

(+)-CPA (optical purity, 63%; 7.3 g) and diethylamine (1.8 g) were added to water (22 ml) and heated to make a solution. The solution was allowed to stand at room temperature overnight. The precipitated crystals were collected by filtration to obtain (+)-CPA/diethylamine (2:1) salt (3.8 g). $[\alpha]_{435}^{18}$ +29.0° (c=1, 99% methanol). Optical purity, 95.1%.

The above obtained (+)-CPA/diethylamine (2:1) salt was decomposed with hydrochloric acid and extracted with ether. Evaporation of the solvent from the ether extract gave (+)-CPA (3.2 g). $[\alpha]_D^{14}$ +45.4° (c=2, chloroform). Optical purity, 94.6%. Yield based on (+)-CPA in the starting CPA, 52.6%.

EXAMPLE 4

(+)-CPA/diethylamine (2:1) salt (optical purity, 40%; 5.8 g) was admixed with water and 2-propanol (1:1 by weight) (10 ml) and heated to make a solution. The solution was allowed to stand at room temperature overnight. The precipitated crystals were collected by filtration to obtain (+)-CPA/diethylamine (2:1) salt (1.9 g). $[\alpha]_{435}^{15}$ (c=1.6, 99% methanol). Optical purity, 93.1%. Yield based on (+)-CPA/diethylamine (2:1) salt in the starting CPA/diethylamine (2:1) salt, 45.2%.

What is claimed is:

1. A method for optical resolution of 2-(4-chlorophenyl)-3-methylbutanoic acid by preferential crystallization, comprising the steps of: (a) crystallizing out the salt of (+) or (−)-2-(4-chlorophenyl)-3-methylbutanoic acid and diethylamine in a molar proportion of 2:1 from a super-saturated solution of the salt of 2-(4-chlorophenyl)-3-methylbutanoic acid with diethylamine; (b) collecting the crystallized salt; and (c) decomposing the collected salt under acidic conditions to obtain the corresponding optically active acid.

2. The method according to claim 1, wherein seed crystals of the salt of (+) or (−)-2-(4-chlorophenyl)-3-methylbutanoic acid and diethylamine in a molar proportion of 2:1 are added to the super-saturated solution.

3. The method according to claim 1, and further comprising the steps of: (d) adding the salt of (+)-2-(4-chlorophenyl)-3-methylbutanoic acid and diethylamine in a molar proportion of 2:1 to the mother liquor after collection of said crystallized salt; (e) crystallizing out the salt of (+) or (−)-2-(4-chlorophenyl)-3-methylbutanoic acid and diethylamine in a molar proportion of 2:1 having an opposite optical activity to that of said crystallized salt as collected in step (b); (f) collecting said crystallized salt of opposite optical activity; and (g) decomposing said collected salt under acidic conditions to obtain the corresponding optically active acid.

4. The method according to claim 1, and further comprising the steps of: (d) adding (+)-2-(4-chlorophenyl)-3-methylbutanoic acid and diethylamine in a molar proportion of 2:1 to the mother liquor after collection of the crystallized salt; (e) crystallizing out the salt of (+) or (−)-2-(4-chlorophenyl)-3-methylbutanoic acid and diethylamine in a molar proportion of 2:1 having an opposite optical activity to that of the crystallized salt as collected in step (b); (f) collecting the crystallized salt of opposite optical activity; and (g) decomposing said collected salt under acidic conditions to obtain the corresponding optically active acid.

5. The method according to claim 3, wherein seed crystals of the salt of (+) or (−)-2-(4-chlorophenyl)-3-methylbutanoic acid and diethylamine in a molar proportion of 2:1 are added to the mother liquor after the addition of the salt between (±)-2-(4-chlorophenyl)-3-methylbutanoic acid and diethylamine in a molar proportion of 2:1 thereto.

6. The method according to claim 4, wherein seed crystals of the salt of (+) or (−)-2-(4-chlorophenyl)-3-methylbutanoic acid and diethylamine in a molar proportion of 2:1 are added to the mother liquor after the addition of (±)-2-(4-chlorophenyl)-3-methylbutanoic acid and diethylamine in a molar proportion of 2:1 thereto.

* * * * *